United States Patent [19]
Schwartz

[11] Patent Number: 5,624,636
[45] Date of Patent: Apr. 29, 1997

[54] HYPOCHLORITE BASED DISINFECTANT FOR DENTAL IMPRESSIONS

[75] Inventor: Richard S. Schwartz, San Antonio, Tex.

[73] Assignee: Univ. of Texas Board of Regents, Austin, Tex.

[21] Appl. No.: 335,439

[22] Filed: Nov. 7, 1994

[51] Int. Cl.$^6$ .................................................. A61L 2/00
[52] U.S. Cl. .............................................. 422/37; 424/661
[58] Field of Search ................... 422/37, 292; 424/661; 252/187.26; 206/5.1

[56] References Cited

U.S. PATENT DOCUMENTS

| | | | |
|---|---|---|---|
| 4,925,017 | 5/1990 | Jessen | 206/5.1 |
| 4,959,220 | 9/1990 | Yamamoto et al. | 424/490 |
| 5,273,678 | 12/1993 | Deroux et al. | 424/661 |
| 5,336,434 | 8/1994 | Park et al. | 424/661 |

OTHER PUBLICATIONS

Bass et al., "The effect of a surface disinfectant on a dental cast," *J. Prosthet. Dent.*, 67(5):723–725, 1992.

Beyerle et al., "Immersion Disinfection of Irreversible Hydrocolloid Impressions With Sodium Hypochlorite. Part I: Microbiology," *Int. J. Prosthodont.*, 7:234–238, 1994.

Christensen et al., "Antimicrobial activity of environmental surface disinfectants in the absence and presence of bioburden," *JADA*, 119:493–505, 1989.

DeWald et al., "Wettability of impression materials treated with disinfectants," *Am. J. Dent.*, 5(2), 103–108, 1992.

Durr et al., "Dimensional Stability of Alginate Impressions Immersed in Disinfecting Solutions," *J. Dent. Child.*, 54(1):45–48, 1987, reprinted in *Trends & Techniques*, Jan./Feb. 1988.

Grabow et al., "Inactivation of Hepatitis A Virus and Indicator Organisms in Water by Free Chlorine Residuals," *Appl. Environ. Microbiol.*, 46(3):619–624, 1983.

Hilton et al., "Immersion Disinfection of Irreversible Hydorcoloid Impressions. Part 2: Effects on Gypsum Casts," *Int. J. Prosthodont.*, 7(5):424–433, 1994.

Jennings et al., "The Persistence of Microorganisms on Impression Materials Following Disinfection," *Int. J. Prosthodont.*, 4(4):382–387, 1991.

Mansfield et al., "Antimicrobial Effects From Incorporation of Disinfectants Into Gypsum Casts," *Int. J. Prosthodont.*, 4(2):180–185, 1991.

Naylor, "Infection Control in Fixed Prosthodontics," *Dental Clinics of North America*, 36(3):809–830, 1992.

Rudd et al., "Sterilization of complete dentures with sodium hypochlorite," *J. Prosthet. Dent.*, 51(3):318–321, 1984.

Rueggeberg et al., "Sodium hypochlorite disinfection of irreversible hydrocolloid impression material," *J. Prosthet. Dent.*, 67(5);628–631, 1992.

Schwartz et al., "Immersion Disinfection of Irreversible Hydrocolloid Impressions. Part 1: Microbiology," *J. Prosthodont. Dent.*, 7:418–423, 1994.

Tan et al., "Effects of disinfecting irreversible hydrocolloid impressions on the resultant gypsum casts: Part I–Surface quality," *J. Prosthet. Dent.*, 69(3):250–257, 1993.

Tan et al., "Effects of disinfecting irreversible hydrocolloid impressions on the resultant gypsum casts: Part II–Dimensional changes," *Prosthet Dent.*, 70(6):532–537, 1993.

Vandewalle et al., "Immersion Disinfection of Irreversible Hydrocolloid Impressions With Sodium Hypochlorite. Part II: Effect on Gypsum," *Int. J. Prosthodont.*, 7(4):315–322, 1994.

Westerholm et al., "Efficacy of Various Spray Disinfectants on Irreversible Hydrocolloid Impressions," *Int. J. Prosthodont.*, 5(1):47–54, 1992.

*Primary Examiner*—Robert J. Warden
*Assistant Examiner*—Krisanne M. Thornton
*Attorney, Agent, or Firm*—Arnold, White & Durkee

[57] ABSTRACT

The invention is directed to improving the disinfection of dental impressions following removal from the patient's mouth and before entering the dental laboratory to prevent contamination. It involves the use of a pH-adjusted hypochlorite solution, which is highly effective in killing microorganisms, and also relatively inexpensive. Using the solution of the instant invention for disinfection causes no damage to the impression, no loss of accuracy, and does not destroy the details on the impression surface.

12 Claims, 1 Drawing Sheet

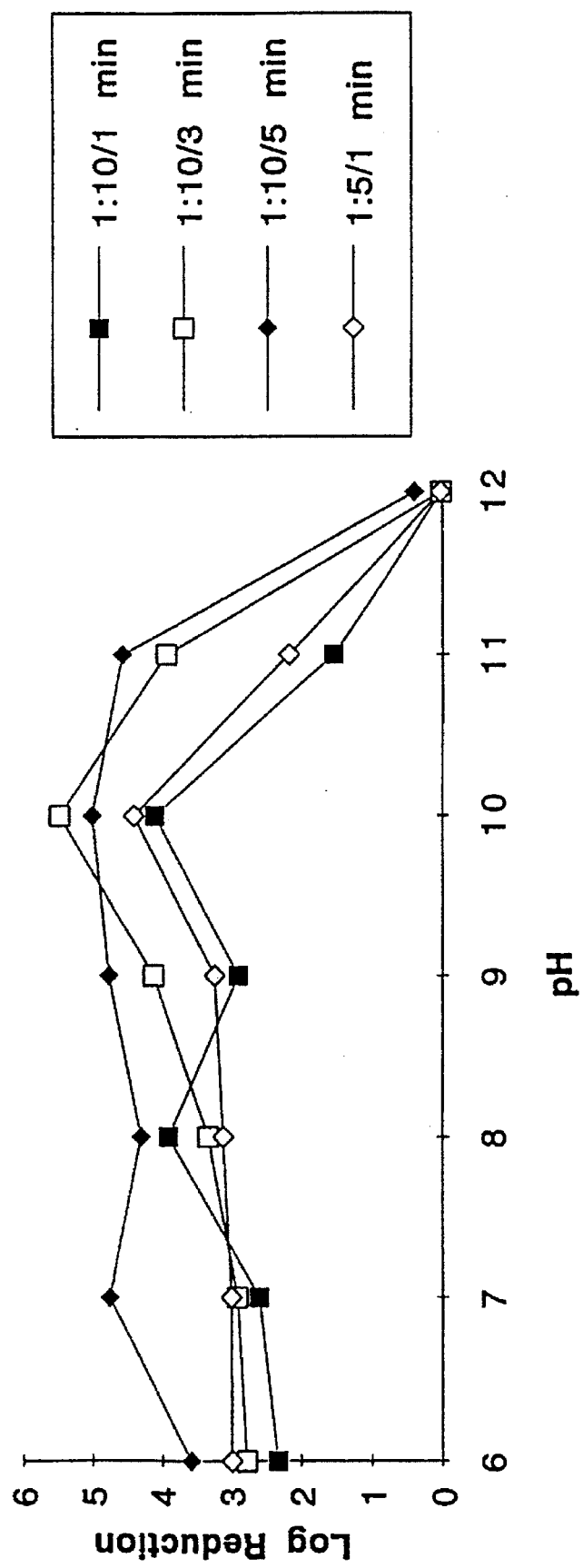

HYPOCHLORITE BASED DISINFECTANT FOR DENTAL IMPRESSIONS

BACKGROUND OF THE INVENTION

1. Field of the Invention

The present invention relates to methods for disinfecting dental impressions. More particularly, it concerns the use of a pH-adjusted hypochlorite solution for killing microorganisms on dental impressions.

2. Description of the Related Art

It has been estimated that over 1,000,000 dental impressions are made each week in the U.S. Impressions are made of the teeth and soft tissues routinely by dentists for the fabrication of crowns, bridges, dentures, orthodontic appliances and many other dental appliances. Gypsum (plaster-like) materials are mixed and poured into the impression and allowed to harden. Once separated from the impression, the gypsum model is an exact duplicate of the patient's teeth and soft tissues. Guidelines from the American Dental Association (ADA), the Centers for Disease Control and Prevention (CDC) and the Occupational Safety and Health Administration (OSHA) require that every impression be disinfected after removal from a patient's mouth and before entering the dental laboratory in order to prevent contamination.

Disinfection of dental impressions is, however, a difficult task. In order to be considered useful, a disinfectant must effectively, and preferably inexpensively, kill the oral microorganisms that are carried on the impression without damaging the impression or reducing its accuracy. Existing disinfectants do not meet these criteria. Glutaraldehydes are often recommended for disinfection of impressions, however they vary greatly in effectiveness and are very expensive. In addition, glutaraldehydes are harmful to living tissue and may induce hypersensitivity, so gloves and other protective gear must be worn by personnel handling them (Naylor, 1992). Iodophores and phenolics are ADA approved for the disinfection of impressions, but are generally ineffective in this application (Westerholm et al., 1992; Schwartz et al., 1994). They have also been found to degrade the surface of some types of impression materials, producing poor quality gypsum models (Hilton et al. 1994). Phenolics are expensive, have a strong odor (requiring a well ventilated work area), and require protective gear (Naylor 1992). All of these disinfectants are less effective than the instant invention, are generally more expensive to manufacture, require longer immersion times, and ultimately produce gypsum models of lesser quality.

One of the least expensive but most effective disinfectants is aqueous sodium hypochlorite, commonly known as bleach. "Hypochlorites" are listed among the ADA's acceptable disinfectants. While sodium hypochlorite is quite effective in its commercially available form, a 5.25% solution in water (Beyerle et al., 1994; Westerholm et al., 1992), such a solution unfortunately etches some impression materials, resulting in a loss of surface detail (Vandewalle, 1994). If the solution is diluted, however, the damage to the impression is eliminated (Vandewalle, 1994), but the result is a concurrent loss of antimicrobial activity (Beyerle et al., 1994). These studies tested standard solutions of sodium hypochlorite, which has an inherent pH of about 12.

None of the products that are currently available for the disinfection of dental impressions are satisfactory. Most ADA approved disinfectants tend to be ineffective (Westerholm 1992; Schwartz et al., 1994) and expensive, cause degradation of some impression materials (Hilton et al., 1994), and have associated safety concerns (Naylor et al., 1992). An impression disinfectant that overcomes these problems would be a major advance in the art.

SUMMARY OF THE INVENTION

The present invention that solves these problems in a surprising and unexpected manner comprises disinfecting dental impressions by contact with an aqueous hypochlorite solution with the pH adjusted to between about 7 and about 11, preferably to about 10. The invention more particularly comprises diluting a concentrated aqueous sodium hypochlorite solution with sufficient water and adding a sufficient quantity of a pH buffer and acid to produce a treating solution containing between about 0.05% and about 1.05% hypochlorite with a pH of about 10. The lower range of hypochlorite concentrations included within the scope of the invention are about 0.05%, 0.1%, 0.2%, 0.3%, and 0.4%. The upper range of hypochlorite concentrations include 0.7%, 0.8%, 0.9%, 1.0% and 1.2%. The hypochlorite solution preferably has a pH between about 7 and about 11. In certain embodiments, a sodium hypochlorite treating solution may be used that contains about 0.5% sodium hypochlorite and has a pH of about 10. As used herein, the term "about" means that, when referring to a pH range, that the value given is able to be varied plus or minus approximately 0.5 pH units. When referring to time units, "about" means that the time may be varied approximately 30 seconds from the stated value.

Sodium hypochlorite is usually supplied as a 5.25% solution with a pH of about 12. It is necessary for stock solutions of hypochlorite to be diluted in order to avoid etching or damaging the surface of the dental impression. This dilution will, however, generally decrease the effectiveness of the disinfectant. To make up for the loss of effectiveness, the inventor studied diluted hypochlorite solutions at lower pH's. It is well documented that lowering the pH of sodium hypochlorite will improve its antimicrobial properties. Previous research performed in test tubes has shown that the optimal pH for antimicrobial activity is about 6 (Block et al., 1991; Clark. 1989; Death, 1979; Russell, 1990; Engelbrecht, 1980). Surprisingly and unexpectedly in view of the literature, the present invention demonstrates that for dental impressions, a pH of about 10 is optimal. A 0.5% sodium hypochlorite solution at pH of approximately 10 has a maximal antimicrobial effect on dental impressions without negative effects on the impression or resultant gypsum models.

A variety of acids or pH buffers may be used to adjust and stabilize the pH of the treating solutions of the invention. Suitable acids include phosphoric, hydrochloric, nitric, sulfuric, or other acids, or salts of acids. For example, in certain embodiments of the present invention, 20N phosphoric acid is used to lower the pH of the hypochlorite solutions. Among the suitable buffers that may be used to stabilize the pH with the present invention are phosphate, borate, carbonate, or citrate.

The amount of time in which the dental impressions will be immersed in the disinfecting solution is of importance. Ideally, that time should be the shortest possible which still disinfects the impression in order to save the dental professional's time and to avoid any possible etching or destruction of the surface detail of the impression.

An especially attractive and economic embodiment of the method of the invention lies in diluting a concentrated commercially available sodium hypochlorite solution to form a treating solution containing from about 0.3% to about 0.7% sodium hypochlorite, with a representative solution having a concentration of hypochlorite of about 0.5%. A widely available hypochlorite solution contains about 5.25% sodium hypochlorite. Diluting such a solution with about ten volumes of water per volume of commercial solution has been found to provide a very effective disinfectant for dental impressions when buffered to a pH between about 7 and about 11.

It is recognized that other hypochlorites, such as potassium, ammonium or alkaline earth hypochlorites may be used within the scope and spirit of the present invention. For example, calcium hypochlorite is available as a powder in the hydrous form and is highly soluble in water. In solution, it derives its antimicrobial property from OCL-HOCL ions, in the same manner as sodium hypochlorite. A 0.6% solution of calcium hypochlorite has approximately the same concentration of OCl⁻/HOCl⁻ as a 0.525% solution of sodium hypochlorite. Such a solution may be made, for example, by adding 6 grams of calcium hypochlorite powder to a liter of water. Since a 0.6% calcium hypochlorite solution and a 0.5% sodium have approximately the same concentration of the active ions, the useful range of concentrations is also about 0.25% to 1.25%. It is also contemplated that aqueous solutions of lithium hypochlorite, potassium hypochlorite, and other solid hypochlorites will be suitable for disinfecting dental impressions. An advantage of solid hypochlorites, such as calcium hypochlorite, is that they are stable in solid form, and therefore shipping and storage costs will be lower than with solution-based hypochlorites.

In related embodiments, the present invention contemplates the preparation of kits that may be employed to contain the necessary ingredients for practicing the invention. Such kits generally comprise individual bottles or vessels that hold the necessary solutions, and instructions for their use.

The container means generally include containers holding the bottles or other vessels, each bottle or vessel containing a solution of sodium hypochlorite and a solution of a suitable acid or buffer, preferably suitably aliquotted. The kits of the present invention also typically include a means for containing the sodium hypochlorite, acid or buffer, and suitable measuring means in close confinement for commercial sale. Such containers may include injection or blow-molded plastic containers into which the desired bottles or vessels are retained.

Kits containing the materials needed for disinfection of dental impressions can be easily made. Such a kit would include a container of concentrated sodium hypochlorite solution, an acid or buffer sufficient to bring the pH to 10, and measuring devices like cups, beakers or droppers to measure the correct amount of each solution as well as water in order to make a disinfecting solution of appropriate sodium hypochlorite concentration and pH.

Hypochlorites which are stable as solids, such as calcium hypochlorite, can be supplied as a power or tablet which is added to water.

The following drawing forms part of the present specification and are included to further demonstrate certain aspects of the present invention. The invention may be better understood by reference to one or more of these drawings in combination with the detailed description of specific embodiments presented herein.

BRIEF DESCRIPTION OF THE DRAWINGS

FIG. 1 is a plot of the mean log reduction in *Bacillus subtilis* bacteria after impressions were disinfected with a sodium hypochlorite solution at various pHs, concentrations, and immersion times. Solid squares are a 1:10 dilution for 1 minute. Open squares are a 1:10 dilution for 3 minutes. Solid diamonds are a 1:10 dilution for 5 minutes. Open diamonds are a 1:5 dilution for 1 minute.

DETAILED DESCRIPTION OF THE PREFERRED EMBODIMENTS

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Reduction of Bacteria With pH Adjusted Sodium Hypochlorite

A series of studies were conducted to evaluate the ADA recommended disinfectants for dental impressions (Westerholm, 1992; Beyerle, 1994, Schwartz, 1994, Hilton, 1994, Vandewalle, 1994). Two of the studies made direct comparisons of the different classes of disinfectants (Westerholm, 1992 and Schwartz, 1994). The conclusion of the studies was that sodium hypochlorite was a promising disinfectant for impressions, but only moderately effective. Subsequent studies attempted to optimize the concentrations and contact times for sodium hypochlorite (Beyerie, 1994; Vandewalle, 1994). Through the efforts of the inventor, it was then established that the antimicrobial activity of such solutions was highest when the pH was lowered to about 10 (Tables 1–3).

All of the studies followed similar protocols. A sterile metal model of a patient's maxillary teeth and soft tissues was contaminated with separate suspensions containing $10^8$ of each of the following organisms: *Pseudomonas aeruginosa, Salmonella choleraesuis, Staphylococcus aureus, Bacillus subtilis*, and *Mycobacterium bovis*. These are the organisms recommended by the Association of Official Analytical Chemists (AOAC) to test whether a disinfectant is bacteriocidal (*P. aeruginosa, S. choleraesuis, S. aureus*), tuberculocidal (*M. bovis*), and sporicidal (*B. subtilis*). Regular set alginate dental impression material (Jeltrate Plus, LD Cauld, Milford, Del.) was hand mixed for 30 seconds using the manufacturer's recommended water-powder ratio and loaded onto a sterilized stock metal tray. An impression was made of the contaminated model and the material was then allowed to bench set for 3 minutes, after which time the model was removed. The impression was then rinsed slowly for 15 seconds with 250 ml of sterile water (Travenol Laboratories, Deerfield, Ill.) in accordance with ADA recommendations. After gently shaking off excess water, viable bacterial transfer was verified by culturing the impression sites of teeth numbers 3 and 14 with a sterile swab soaked in D/E Neutralizing Broth (Becton-Dickinson Microbiology Systems, Cockeysville, Md.). These cultures were plated onto Trypticase Soy Agar (TSA) and incubated aerobically at 37° C. for 48 hours, except for *M. bovis*, which was plated onto 7H11 agar and incubated at 37° C. aerobically for up to 21 days. The impression was then immersed in the appropriate dilution of one of the disinfectants for contact times of 1, 2, 3, 5, or 10 minutes.

Immediately following the prescribed contact time, the impression was removed from the disinfectant, rinsed again with 250 ml of sterile water, and gently shaken to remove excess disinfectant and water. The occlusal surface/cusp tips of teeth numbers 2 and 15 in the impression were then cultured exactly as done before the disinfection step. This procedure was repeated until six impressions contaminated with each microorganism had been tested using each disinfectant. Fresh disinfectant was used for each impression. As a control, six impressions per organism were treated with sterile water. After incubation, all plates were examined for growth, and standard microbiological methods were used to identify and enumerate recovered bacteria. Colony forming units (CFUs) for each bacterium were determined before and after disinfection, and reductions in CFUs were calculated and converted to logs.

The five test organisms generally followed the expected pattern of resistance to chemical agents. Three of the bacterial species, *P. aeruginosa*, *S. choleraesuis*, and *S. Aureus* (all human pathogens) had little resistance to most of the disinfectant solutions. Thus, these organisms could not be used to determine differences in effectiveness of the disinfectants. *M. bovis* (a "safer" version of M. tuberculosis, a very resistant bacterium) was somewhat resistant to the disinfectants. *B. subtilis* (a strain commonly used to test sterilizers and disinfectants) was generally the most resistant organism. Therefore, to evaluate the maximal effectiveness of the disinfectants, only *M. bovis* and *B. subtilis* were used in later studies.

Although various standards have been suggested, it is generally accepted that a 4 log or greater reduction in bacteria is effective disinfection. This corresponds to the destruction of greater than 99.99% of the treated bacteria. For example, if a sample has 1,000,000 bacteria per ml, a 4 log reduction would reduce it to 100 bacteria per ml.

Immersion of the dental impressions in the full strength hypochlorite solution for one minute was quite effective, but the surface quality of some of the gypsum models was degraded. Compared to a 1:10 dilution and a water control, surface roughness was significantly increased (as measured on a profilometer), and detail reproduction was significantly worse (using the ANSI/ADA Specification No. 18 test). Thus, it can be said that a full strength sodium hypochlorite solution is not suitable for use with all dental products (Vandewalle, 1994).

The results show that dilutions of sodium hypochlorite are not as effective as the full strength solution (Beyerie, 1994). By lowering the pH of diluted sodium hypochlorite by addition of 20N phosphoric acid, however, the effectiveness is greatly increased. FIG. 1 presents a plot of the results for *Bacillus subtilis* with varying pH, immersion time, and hypochlorite concentration. As indicated in this figure, the universal peak activity is found when the pH is adjusted to a value of 10, although pH values of 7–11 are also effective for immersion times longer than one minute.

Tables 1 and 2 present the mean log reduction of *Bacillus subtilis* and *Mycobacterium bovis* as a function of pH for the 1:10 dilution at various immersion times.

TABLE 1

1:10 Bleach vs. *B. Subtilis* (Log Reductions)

| | | Individual Impressions | | | | | | Mean |
|---|---|---|---|---|---|---|---|---|
| pH 12 | 10 min | 0.96 | 0.77 | 0.34 | 1.69 | 1.47 | 1.05 | 1.05 |
| | 5 min | 0.72 | 0.26 | 0.42 | 0.17 | 0.06 | 0.69 | 0.39 |
| | 1 min | 0.00 | 0.00 | 0.00 | 0.00 | 0.07 | 0.00 | 0.01 |
| pH 11 | 10 min | 5.51 | 4.73 | 4.92 | 4.15 | 5.56 | 4.95 | 4.97 |
| | 5 min | 5.03 | 3.15 | 3.00 | 5.23 | 5.37 | 5.58 | 4.56 |
| | 1 min | 1.46 | 1.36 | 1.68 | — | 2.13 | 1.01 | 1.53 |
| pH 10 | 10 min | 4.63 | 4.60 | 5.42 | 5.16 | 5.38 | 5.30 | 5.08 |
| | 5 min | 4.42 | 4.51 | 5.47 | 5.60 | 4.78 | 5.24 | 5.00 |
| | 3 min | 5.21 | 5.62 | 5.36 | 5.38 | 5.59 | 5.67 | 5.47 |
| | 2 min | 4.94 | 5.57 | 5.72 | 2.30 | 5.43 | 2.65 | 4.43 |
| | 1 min | 4.50 | 5.50 | 4.33 | 3.53 | 3.93 | 2.82 | 4.10 |
| pH 9 | 10 min | 5.55 | 4.40 | 5.76 | 5.47 | 5.37 | 5.34 | 5.32 |
| | 5 min | 5.70 | 3.56 | 2.90 | 5.50 | 5.34 | 5.48 | 4.76 |
| | 1 min | 3.03 | 3.47 | 2.48 | 2.77 | 3.31 | 2.42 | 2.91 |
| pH 8 | 10 min | 4.69 | 5.37 | 5.44 | 4.30 | 5.27 | 4.25 | 4.89 |
| | 5 min | 5.37 | 3.52 | 3.46 | 4.35 | 4.35 | 4.74 | 4.30 |
| | 1 min | 3.55 | 3.57 | 2.67 | 5.26 | 4.89 | 3.52 | 3.91 |
| pH 7 | 10 min | 5.41 | 5.33 | 5.37 | 4.78 | 4.98 | 4.76 | 5.11 |
| | 5 min | 5.27 | 2.83 | 5.29 | 5.23 | 5.40 | 4.49 | 4.75 |
| | 1 min | 2.24 | 2.57 | 2.93 | 4.36 | 2.00 | 2.71 | 2.80 |
| pH 6 | 10 min | 4.25 | 5.32 | 4.82 | 4.12 | 3.68 | 2.83 | 4.17 |
| | 5 min | 3.66 | 5.45 | 3.49 | 4.11 | 2.07 | 2.69 | 3.58 |
| | 1 min | 3.61 | 2.43 | 2.10 | 2.22 | 2.36 | 1.26 | 2.33 |
| Water | | | | | | | | |
| pH 6 | 10 min | 0.00 | 0.00 | 0.00 | | | | 0.00 |
| pH 10 | 10 min | 0.25 | 0.07 | 0.00 | | | | 0.11 |

Bold numbers are impressions which had less than a 4 log reduction but are in groups with a mean of 4 logs or greater.

Bold numbers are impressions which had less than a 4 log reduction but are in groups with a mean of 4 logs or greater.

TABLE 2

1:10 Bleach vs. *M. bovis* (Log Reductions)

| | | Individual Impressions | | | | | | Mean |
|---|---|---|---|---|---|---|---|---|
| pH 12 | 10 min | 0.94 | 0.82 | 0.66 | 0.88 | 0.59 | 0.75 | 0.77 |
| | 5 min | 0.56 | 0.72 | 0.85 | 0.72 | 0.54 | 0.28 | 0.61 |
| | 1 min | 0.00 | 0.28 | 0.22 | 0.19 | 0.08 | 0.16 | 0.16 |
| pH 11 | 10 min | 5.39 | 5.16 | 5.04 | 4.93 | 5.04 | 4.03 | 5.08 |
| | 5 min | 5.16 | 5.05 | — | 5.01 | 4.90 | 4.92 | 5.01 |
| | 1 min | 1.38 | 1.98 | 1.50 | 2.15 | 2.33 | 2.32 | 1.94 |
| pH 10 | 10 min | 5.50 | 5.48 | 5.28 | 5.42 | 5.80 | 5.37 | 5.48 |
| | 5 min | 5.21 | 5.18 | 5.20 | 5.21 | 5.29 | 5.10 | 5.20 |
| | 3 min | 5.54 | 5.26 | 5.22 | 4.38 | 5.29 | 4.88 | 5.10 |
| | 2 min | 5.55 | 4.55 | 5.24 | 5.33 | 5.18 | 4.53 | 5.06 |
| | 1 min | 4.09 | 2.45 | 4.42 | 3.52 | 1.95 | 2.38 | 3.14 |
| pH 9 | 10 min | 5.63 | 5.75 | 5.63 | 5.75 | 4.91 | 5.37 | 5.51 |
| | 5 min | 3.96 | 2.78 | 4.61 | 5.60 | 4.96 | 4.80 | 4.45 |
| | 1 min | 5.27 | 5.32 | 3.74 | 3.06 | 3.78 | 5.33 | 4.42 |
| pH 8 | 10 min | 5.25 | 5.60 | 5.43 | 5.46 | 5.53 | 5.20 | 5.41 |
| | 5 min | 5.48 | 4.25 | 4.78 | 5.26 | 5.35 | 5.44 | 5.09 |
| | 1 min | 5.30 | 3.37 | 4.72 | 5.10 | 5.02 | 2.16 | 4.26 |
| pH 7 | 10 min | 5.39 | 5.35 | 5.20 | 5.06 | 5.30 | 5.36 | 5.28 |
| | 5 min | 5.24 | 5.39 | 4.93 | 5.28 | 4.82 | 5.28 | 5.14 |
| | 1 min | 2.64 | 5.39 | 4.55 | 2.24 | 3.40 | 5.34 | 3.93 |
| pH 6 | 10 min | 5.66 | 5.65 | 5.17 | 5.39 | 5.09 | 5.33 | 5.38 |
| | 5 min | 5.39 | 5.92 | 5.42 | 5.31 | 5.26 | 5.44 | 5.46 |
| | 1 min | 5.21 | 2.53 | 2.47 | 4.60 | 2.72 | 5.98 | 3.92 |
| Water | | | | | | | | |
| pH 6 | 10 min | 0.05 | 0.00 | 0.00 | | | | 0.02 |
| pH 10 | 10 min | 0.00 | 0.21 | 0.00 | | | | 0.07 |

Bold numbers are impressions which had less than a 4 log reduction but are in groups with a mean of 4 logs or greater.

Bold numbers are impressions which had less than a 4 log reduction but are in groups with a mean of 4 logs or greater.

Although several pHs produced a mean reduction of greater than 4 logs, only pH 10 consistently produced a 4 log reduction with *B. subtilis* at times of 3 minutes or longer. It is important that a disinfectant provides a consistent high level of antimicrobial activity, not just a high average. The less resistent organism, *M. bovis*, had consistently high levels of reduction at several pHs and times longer than one minute.

Table 3 shows the effects of various pHs and immersion times on the surface roughness of gypsum specimens recovered from disinfected impressions. A total of 10 gypsum specimens were made at each pH and each immersion time. Ra (roughness average) values increase (the surface becomes rougher) as the pH of sodium hypochlorite decreases. Ra is also time dependent. With 3 and 5 minute immersion times the Ra value is comparable (based on statistical analysis) to the water control. The 10 minute groups are significantly rougher than the control (again, based on statistical analysis).

TABLE 3

EFFECT OF PH ON GYPSUM SURFACE ROUGHNESS

| pH | Immersion time | Ra |
|---|---|---|
| Control (water) | Rinse | 1.13* |
| 11.5 | 10 min | 1.78 |
| 10 | 10 min | 2.06 |
| 8 | 10 min | 2.15 |
| 10 | 5 min | 1.34* |
| 10 | 3 min | 1.19* |

*Groups which are statistically equivalent

As shown in these results, sodium hypochlorite may be optimized as a disinfectant for dental impressions when the solution is diluted to approximately 0.5% and the pH is adjusted to around 10. An immersion time of approximately 3 minutes will produce highly effective disinfection without negative effects on the impression material or resultant gypsum models. Higher concentrations are also effective antimicrobials, but cause degradation of some types of gypsum materials. Likewise, as the pH is lowered below 10, the gypsum models tend to exhibit a progressive loss of quality.

EXAMPLE 2

A Kit For Dental Impression Disinfection

A kit for disinfecting dental impressions consists of a large bottle of aqueous sodium hypochlorite, preferably in a concentration of 0.05% to 5.25%, and another smaller bottle or vessel with an acid or buffer solution. Measuring devices are included in order to correctly measure the amount of each solution and the water needed for the desired concentration and pH value. Measuring devices may include cups, beakers, droppers, or similar means.

A typical procedure would involve first pouring the sodium hypochlorite into a measuring device. Water is then added to dilute the sodium hypochlorite solution to the desired concentration. Finally, a specified amount of acid or buffer solution is added to obtain the correct pH.

Alternatively, the hypochlorite solution may be prediluted to the proper concentration , for example at between 0.05% and 1.05%, and packaged in a bottle with space left for buffer addition. This diluted solution is adjusted to the proper pH by adding a premeasured amount of acid or buffer sufficient to adjust the hypochlorite solution to the proper pH.

All of the compositions and methods disclosed and claimed herein can be made and executed without undue experimentation in light of the present disclosure. While the compositions and methods of this invention have been described in terms of representative embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Block, S.S. and Dychdala, G.R., *Disinfection, Sterilization, and Preservation,* 4th Ed., Lea and Febiger, Philadelphia, 135–36 (1991).

Beyerle, M., Hensley, D.H., Bradley, D.V. Jr., Schwartz, R.S., Hilton, T.J., Int. *J. Prosthodont.* 7, 234–238 (1994).

Christiansen, R.P., Robinson, R.A., Robinson, D.F., Ploeger, B.J., Leavitt, R.W., and Bodily, H.L., *J. Amer. Dental Assn.* 119, 493–505 (1989).

Clark, R.M., Read, E.J. and Hoff, J.C., *J. Environ. Engineer* 115, 80–90 (1989).

Death, J.E. and Coats, D., *J. Clin. Pathol.* 32, 148–53, (1979).

Engelbrecht, R.S., Weber, J.J., Salter, B.L. and Schmidt, C.A., *Appl. Environ. Microbiol.* 40, 249–56 (1980).

Grobow, W.O.K., Gauss-Muller, V., Proxesky, O.W. and Deinhardt, F., *Appl. Environ. Microbiol.* 46, 619–24 (1983).

Hilton, T.J., Schwartz, R.S., Bradley, D.V. Jr., *Int. J. Prosthodont.* 7, 424–433 (1994).

Naylor, W.P., *Dental Clinics of North America* 36, 809–830 (1992).

Prince, H.N., *Particulate and Microbial Control,* March/April, 55–62 (1983).

Richardson, W.L., Technical Report (1989, NNDC-TR-103 (Abstract No. 16):13.

Russell, A.D., *Clin. Micro. Rev.* 3, 99–119, (1990).

Schwartz, R.S., Bradley, D.V. Jr., Hilton, T.J., Kruze, S.K. *Int. J. Prosthodont.*, 7, 418–423 (1994).

Vandewalle, K.S., Charlton, D.G., Schwartz, R.S., Reagan, S.E. and Koeppen, R.G., *Int. J. Prosthodont.* 7, 315–322 (1994).

Westerholm, H. S. , Bradley, D.V. Jr. , and Schwartz, R.S. , *Int. J. Prosthet.* 5, 47–54 (1992) .

What is claimed is:

1. A method of disinfecting a dental impression comprising providing a dental impression, and contacting the impression with an aqueous hypochlorite solution having a pH between about 9 and about 11 for a period sufficient to cause at least a 4 log reduction in microorganisms said period being from about 1 minute to about 5 minutes.

2. The method of claim 1 in which the hypochlorite comprises sodium hypochlorite.

3. The method of claim 1 in which the pH is about 10.

4. A method of disinfecting a dental impression which comprises providing a dental impression, and contacting the impression with an aqueous solution having a pH between about 9 and about 11 and wherein said solution contains between about 0.05% and about 1.05% sodium hypochlorite, said contacting to be for a period of about 1 minute to about 5 minutes.

5. The method of claim 1 wherein the solution contains between about 0.05% and about 1.05% sodium hypochlorite.

6. The method of claim 5 wherein the solution contains about 0.5% sodium hypochlorite.

7. The method of claim 4 wherein the solution contains about 0.525% sodium hypochlorite.

8. A method of disinfecting a dental impression which comprises:

a) mixing an aqueous solution containing about 5.25% sodium hypochlorite with sufficient water and a sufficient quantity of a pH buffer to produce an aqueous treating solution having a pH between about 9 and about 11, and containing about 0.525% sodium hypochlorite; and b) contacting the dental impression for a period of about 1 minute to about 5 minutes with the treating solution under conditions to disinfect the dental impression.

9. The method of claim 1, wherein the dental impression comprises an alginate material.

10. The method of claim 4, wherein the dental impression comprises an alginate material.

11. The method of claim 8, wherein the dental impression comprises an alginate material.

12. A method of disinfecting an elginate dental impression comprising:

providing an alginate dental impression; and contacting the impression with an aqueous solution containing about 0.525% sodium hypochlorite and having a pH between about 9 and about 11, said contacting to be for a period of about 1 minute to about 5 minutes to cause at least a 4 log reduction in microorganisms.

* * * * *